(12) United States Patent
Zaveri et al.

(10) Patent No.: US 11,951,203 B2
(45) Date of Patent: Apr. 9, 2024

(54) DEEP WRINKLE VANISHING COMPOSITIONS

(71) Applicants: Chanda Zaveri, Rancho Palos Verdes, CA (US); Meng Teng Lim, Island East (HK)

(72) Inventors: Chanda Zaveri, Rancho Palos Verdes, CA (US); Meng Teng Lim, Island East (HK)

(*) Notice: Subject to any disclaimer, the term of this patent is extended or adjusted under 35 U.S.C. 154(b) by 0 days.

(21) Appl. No.: 17/003,652

(22) Filed: Aug. 26, 2020

(65) Prior Publication Data

US 2022/0062143 A1    Mar. 3, 2022

(51) Int. Cl.

| | | |
|---|---|---|
| *A61K 8/64* | (2006.01) | |
| *A61K 8/11* | (2006.01) | |
| *A61K 8/44* | (2006.01) | |
| *A61K 8/73* | (2006.01) | |
| *A61K 9/00* | (2006.01) | |
| *A61K 9/48* | (2006.01) | |
| *A61K 31/197* | (2006.01) | |
| *A61K 31/401* | (2006.01) | |
| *A61K 38/05* | (2006.01) | |
| *A61K 38/08* | (2019.01) | |
| *A61K 47/38* | (2006.01) | |
| *A61P 17/00* | (2006.01) | |
| *A61Q 19/08* | (2006.01) | |

(52) U.S. Cl.
CPC .................. *A61K 8/64* (2013.01); *A61K 8/11* (2013.01); *A61K 8/44* (2013.01); *A61K 8/731* (2013.01); *A61K 8/732* (2013.01); *A61K 9/0053* (2013.01); *A61K 9/4833* (2013.01); *A61K 31/197* (2013.01); *A61K 31/401* (2013.01); *A61K 38/05* (2013.01); *A61K 38/08* (2013.01); *A61K 47/38* (2013.01); *A61P 17/00* (2018.01); *A61Q 19/08* (2013.01); *A61K 2800/92* (2013.01)

(58) Field of Classification Search
None
See application file for complete search history.

(56) References Cited

U.S. PATENT DOCUMENTS

| | | | | |
|---|---|---|---|---|
| 2010/0055138 | A1* | 3/2010 | Margulies | A61K 31/74 424/401 |
| 2010/0331274 | A1* | 12/2010 | Gupta | A61K 31/715 514/47 |
| 2017/0224760 | A1* | 8/2017 | Garruto | A61K 47/186 |
| 2021/0236406 | A1* | 8/2021 | Kim | A61K 8/27 |

FOREIGN PATENT DOCUMENTS

| | | | |
|---|---|---|---|
| KR | 102120992 B1 * | 6/2020 | |
| KR | 1020200049122 A * | 7/2020 | |
| WO | WO-2018113891 A1 * | 6/2018 | ............... C07K 5/06 |

OTHER PUBLICATIONS

Rud, "Dermatologists say Argireline basically performs just like botox", Byrdie, 2019. pp. 1-6. (Year: 2019).*
Bojarska, Amino Acids and Short Peptides as Anti-Aging "Superfood", Int J Nutr Sci. 2020; 5(1):1039. Published on Jun. 5, 2020 (Year: 2020).*
Cayman Chemical, "Product Information, Acetyl Hexapeptide-3 (acetate)", 2019, p. 1. (Year: 2019).*
Blanchevoye et al. "Interaction between the Elastin Peptide VGVAPG and Human Elastin Binding Protein." Journal of Biological Chemistry, American Society for Biochemistry and Molecular Biology, 2013, 288 (2), pp. 1317-1328.

* cited by examiner

*Primary Examiner* — Kyung S Chang
(74) *Attorney, Agent, or Firm* — Elevated IP, LLC

(57) ABSTRACT

The present invention relates to compositions and methods for reducing or eliminating wrinkles and improving skin texture and appearance. The compositions, which comprise at least one acetyl hexapeptide and a dipeptide that is optionally complexed to an amino acid, may be administered orally, sublingually, topically and/or transdermally.

17 Claims, No Drawings

DEEP WRINKLE VANISHING COMPOSITIONS

CROSS-REFERENCE TO RELATED APPLICATIONS

None.

BACKGROUND

Large sums of money are spent each year in an effort to reduce signs of aging. However, botulinum toxin injections, dermal fillers, laser treatments, cosmetic surgery and many other products and services are expensive, painful and temporary. Additionally, although less invasive, the repetitive use of topical products, such as retinoic acid, is also costly and dermally irritating. Yet the desire for a youthful appearance drives consumers to accept recovery periods lasting days to months with various levels of bruising, bleeding, pealing, stinging and other side effects that look and feel unpleasant. Unfortunately, there are very few efficacious, painless and cost-effective products for reducing wrinkles and improving skin texture.

SUMMARY

The present invention relates to compositions and methods for reducing or eliminating wrinkles and improving skin texture and appearance. The compositions, which comprise at least one acetyl hexapeptide and a dipeptide that is optionally complexed to an amino acid, may be administered orally, sublingually, topically and/or transdermally.

In an aspect, a composition comprises at least one acetyl hexapeptide and a dipeptide having a sequence of Lys-Pro in a cosmetically or pharmaceutically acceptable carrier. For example, the at least one acetyl hexapeptide, as identified by its INCI (International Nomenclature of Cosmetic Ingredients) name, may be selected from the group consisting of acetyl hexapeptide-1, acetyl hexapeptide-3, acetyl hexapeptide-7, acetyl hexapeptide-8, acetyl hexapeptide-19, acetyl hexapeptide-20, acetyl hexapeptide-22, acetyl hexapeptide-24, acetyl hexapeptide-30, acetyl hexapeptide-31, acetyl hexapeptide-37, acetyl hexapeptide-38, acetyl hexapeptide-39, acetyl hexapeptide-46 and acetyl hexapeptide-49.

In an embodiment, the at least one acetyl hexapeptide is present in a concentration between 2 wt % and 30 wt %, or between 5 wt % and 28 wt %, or between 10 wt % and 25 wt %, or between 15 wt % and 25 wt %, or between 20 wt % and 25 wt %. In an embodiment, the at least acetyl hexapeptide is present in a concentration of at least 5 wt %, or at least 10 wt %, or at least 15 wt %, or at least 20 wt %, or at least 22 wt %, or at least 25 wt %.

In an embodiment, the at least one acetyl hexapeptide and the dipeptide are present in a weight ratio between 5:1 and 20:1, or between 7:1 and 15:1, or between 9:1 and 12:1. In an embodiment, the at least one acetyl hexapeptide and the dipeptide are present in a weight ratio of 5:1, 7:1, 9:1 11:1, 12:1, 15:1 or 20:1.

In an embodiment, a composition disclosed herein further comprises at least two acetyl hexapeptides or at least three acetyl hexapeptides.

In an embodiment, a composition disclosed herein further comprises an amino acid selected from the group consisting of glycine, alanine, proline and combinations thereof. In an embodiment, the amino acid is complexed with the dipeptide. In an embodiment, the amino acid and the dipeptide are covalently bound to one another, or the amino acid and the dipeptide are ionically bound to one another, or the amino acid and the dipeptide are electrostatically attracted to one another. In an embodiment, a weight ratio of dipeptide to amino acid in a complex is 2:1.

In an embodiment, a composition disclosed herein is enclosed within a capsule. For example, the capsule may be a gelatin capsule, a starch capsule, a hydroxy propyl methyl cellulose (HMPC) capsule, or a hydroxy propyl cellulose (HPC) capsule.

In an embodiment, a cosmetically or pharmaceutically acceptable carrier suitable for use in a disclosed composition is selected from the group consisting of water, an organosilicone compound, a silicone elastomer, a $C_6$-$C_{28}$ linear hydrocarbon and combinations thereof.

In an aspect, a method of reducing skin wrinkling in a subject in need thereof comprises administering to the subject a therapeutically effective amount of a composition comprising at least one acetyl hexapeptide and a dipeptide having a sequence of Lys-Pro in a cosmetically or pharmaceutically acceptable carrier.

In an embodiment, a therapeutically effective amount is administered in portions once daily, twice daily or three times daily. For example, the composition may be administered at a daily dose of 20 mg/kg/day to 50 mg/kg/day.

In an embodiment, the composition is administered orally or sublingually, for example, in the form of an oral spray, an emulsion, a tincture, a syrup, a food additive or a capsule. As such, a method of reducing skin wrinkling in a subject may further comprise loading the composition into a capsule.

In an embodiment, the composition is administered topically or transdermally, for example, in the form of a lotion, an oil, a cream, or a serum.

DETAILED DESCRIPTION

In general, the terms and phrases used herein have their art-recognized meaning, which can be found by reference to standard texts, journal references and contexts known to those skilled in the art. The following definitions are provided to clarify their specific use in the context of this description.

An "amino acid" is a molecular building block of protein. An "amino acid residue" is the simplest discreet unit or monomer of a protein chain.

A "complex" is a chemical entity formed by coupling (e.g., electrostatically) or bonding (e.g., covalently or ionically) two molecules.

In an embodiment, a "serum" is a product with a high concentration of active substances that are rapidly absorbed. Skincare serums are typically applied topically after cleansing and before moisturizing.

A new signal sequence, particularly, a dipeptide that improves transdermal delivery and/or absorption of acetyl hexapeptides is disclosed herein. The new signal sequence has the amino acid sequence:

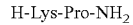

H-Lys-Pro-$NH_2$

Standard three letter codes are used to designate the amino acids. Accordingly, the dipeptide above contains the amino acids: Lysine-Proline Methods of Dipeptide Synthesis One method of producing a dipeptide involves chemical synthesis. This can be accomplished using solid phase methodologies well known to those skilled in the art. (See, e.g., Stewart, J. M. & Young, J. D. "Solid Phase Peptide Synthesis" Pierce Chemical Co. Rockford, Ill. 1984; Merrifield, J. Am. Chem. Soc., 85:2149 1964; Houghten, Proc.

Natl. Acad. Sci. USA 82:5132 1985; and U.S. Pat. Nos. 4,105,603; 3,972,859; 3,842,067; and 3,862,925).

The condensation between two amino acids, or an amino acid and a peptide, or a peptide and a peptide can be carried out according to the usual condensation methods such as the azide method, mixed acid anhydride method, DCC (N,N-dicyclohexylcarbodiimide) or DIPC (N,N'-diisopropylcarbodiimide) methods, active ester method (p-nitrophenyl ester method), BOP benzotriazole-1-yl-oxy-tris (dimethylamino) phosphonium hexafluorophosphate method, N-hydroxysuccinic acid imido ester method, etc., and Woodward reagent K method.

Amino Acid Substitutions

It is a well established principle of protein and peptide chemistry that certain amino acid substitutions, entitled "conservative" amino acid substitutions, can frequently be made in a protein or a peptide without altering either the conformation or the function of the protein or peptide. Conservative substitutions may be employed in the synthesis of proteins, peptides or analogs disclosed herein. Accordingly, peptides having conservative amino acid substitutions are within the scope of the present invention. Such changes include substituting any of isoleucine (I), valine (V), and leucine (L) for any other of these amino acids; aspartic acid (D) for glutamic acid (E) and vice versa; glutamine (0) for asparagine (N) and vice versa; and serine (S) for threonine (T) and vice versa. The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine and valine. Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Cysteine (C) can frequently be replaced by serine (S) when cysteine's capacity to form disulfide bonds is either undesirable or unneeded. Still other changes can be considered "conservative" in particular environments.

Cosmetic and Pharmaceutical Compositions

In general, a cosmetic or pharmaceutical composition of the present invention comprises an acetyl hexapeptide and a dipeptide in a therapeutically effective amount and an acceptable carrier, excipient or diluent.

The therapeutically effective amount can be determined by one of ordinary skill in the art, with reference to the dosages described herein.

Conventional acceptable carriers known in the art can include alcohols, e.g., ethyl alcohol, serum proteins, cholesterol, human serum albumin, liposomes, buffers such as phosphates, water, sterile saline or other salts, electrolytes, glycerol, hydroxymethylcellulose, propylene glycol, polyethylene glycol, polyexyethylenesorbitan, other surface active agents, vegetable oils, and conventional anti-bacterial or anti-fungal agents, such as parabens, chlorobutanol, phenol, sorbic acid, and the like. A cosmetically acceptable carrier or a pharmaceutically acceptable carrier within the scope of the present invention meets industry standards for sterility, isotonicity, stability, and non-pyrogenicity. In an embodiment, a cosmetically or pharmaceutically acceptable carrier suitable for use in a disclosed composition is selected from the group consisting of water, an organosilicone compound, a silicone elastomer, a $C_6$-$C_{28}$ linear hydrocarbon and combinations thereof.

The active ingredient is often mixed with diluents or excipients that are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like. For a more detailed description of the foregoing see a standard pharmaceutical text such as Remington's Pharmaceutical Sciences, Mack Publishing Co. Easton, Pa. (1970).

Methods of Use

The compounds of this invention are shown to reduce or eliminate wrinkles and improve skin texture and appearance.

Administration

Compositions according to the present invention can be administered by a number of routes. They are typically administered topically, transdermally, orally or sublingually. In an embodiment, oral administration may be accomplished by delivering a liquid in capsule form.

The dosages to be administered can be determined by one of ordinary skill in the art depending on the clinical severity of the condition, the age, sex and weight of the patient, the exposure of the patient to conditions that may affect the course of wrinkle treatment, the existence or nonexistence of underlying systemic problems such as diabetes, impaired circulation, and immunocompromised status, and other pharmacokinetic factors generally understood in the art, such as liver and kidney metabolism. The interrelationship of dosages for animals of various sizes and species and humans based on mg/m 3 of surface area is described by E. J. Freireich et al., "Quantitative Comparison of Toxicity of Anticancer Agents in Mouse, Rat, Hamster; Dog, Monkey and Man," Cancer Chemother. Rep. 50:219-244 (1966). Adjustments in the dosage regimen can be made to optimize the therapeutic response. Doses can be divided and administered on a daily basis or the dose can be reduced proportionally depending on the therapeutic situation.

Methods according to the present invention can be used to treat humans or socially or economically important animal species such as dogs, cats, horses, sheep, cows, goats, or pigs. Methods according to the present invention are not limited to use in humans.

The invention is illustrated by the following Example. This Example is for illustrative purposes only and is not intended to limit the invention.

EXAMPLE

This Example provides an exemplary composition for reducing or eliminating wrinkles and improving skin texture.

TABLE 1

Deep wrinkle vanishing composition.

| Ingredient | Concentration (wt %) |
|---|---|
| Deionized Water | qs |
| Acetyl hexapeptide-24 amide or Acetyl hexapeptide-51 amide | 10 |
| Acetyl hexapeptide-8 | 10 |
| Cyclopentasiloxane | 7 |
| Dimethicone cross polymer | 6 |
| Ethylhexyl cocoate | 5 |
| BIS-peg/ppg - 14/14m dimethicone | 4 |
| Stearyl dimethicone | 4 |
| Octadecene/1-Octadecene | 4 |

TABLE 1-continued

Deep wrinkle vanishing composition.

| Ingredient | Concentration (wt %) |
|---|---|
| Acetyl hexapeptide-3 | 2 |
| Palmitoyl pentapeptide-5 or Palmitoyl tripeptide-5 | 2 |
| Lys-Pro, Gly complex | 2 |

The exemplary composition may be made by combining the ingredients in Table 1 in a single vessel. The ingredients may be added in any order and mixed by magnetic or mechanical stirring (e.g., paddle, whisk, rotary screw) at medium to high speed for between 5 minutes and 1 hour until evenly distributed.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, and method steps set forth in the present description. As will be apparent to one of skill in the art, methods and devices useful for the present methods and devices can include a large number of optional composition and processing elements and steps.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a peptide" includes a plurality of such peptides and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is/are not specifically disclosed herein.

All art-known functional equivalents of materials and methods are intended to be included in this disclosure. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed can be resorted to by those skilled in the art, and that such modifications and variations are considered to be within the scope of this invention as defined by the appended claims.

What is claimed is:

1. A composition comprising a first acetyl hexapeptide, a second acetyl hexapeptide, ethylhexyl cocoate, and a dipeptide having a sequence of Lys-Pro in a cosmetically or pharmaceutically acceptable carrier wherein the first acetyl hexapeptide is selected from the group consisting of acetyl hexapeptide-1, acetyl hexapeptide-3, acetyl hexapeptide-7, acetyl hexapeptide-8, acetyl hexapeptide-19, acetyl hexapeptide-20, acetyl hexapeptide-22, acetyl hexapeptide-24, acetyl hexapeptide-30, acetyl hexapeptide-31, acetyl hexapeptide-37, acetyl hexapeptide-38, acetyl hexapeptide-39, acetyl hexapeptide-46 and acetyl hexapeptide-49, wherein the second acetyl hexapeptide is selected from the group consisting of acetyl hexapeptide-1, acetyl hexapeptide-7, acetyl hexapeptide-20, acetyl hexapeptide-22, acetyl hexapeptide-30, acetyl hexapeptide-31, acetyl hexapeptide-37, acetyl hexapeptide-38, acetyl hexapeptide-39, acetyl hexapeptide-46, acetyl hexapeptide-49 and acetyl hexapeptide-51 amide, and wherein the first acetyl hexapeptide and the dipeptide are present in a weight ratio between 5:1 and 20:1.

2. The composition of claim 1, wherein the first acetyl hexapeptide is present in a concentration between 2 wt % and 30 wt %.

3. The composition of claim 1, wherein the first acetyl hexapeptide and the dipeptide are present in a weight ratio of 11:1.

4. The composition of claim 1, further comprising an amino acid selected from the group consisting of glycine, alanine, proline and combinations thereof.

5. The composition of claim 4, wherein the amino acid is complexed with the dipeptide.

6. The composition of claim 1 enclosed within a capsule.

7. The composition of claim 1, wherein the cosmetically or pharmaceutically acceptable carrier is selected from the group consisting of water, an organosilicone compound, a silicone elastomer, a $C_6$-$C_{28}$ linear hydrocarbon and combinations thereof.

8. A method of reducing skin wrinkling in a subject in need thereof, said method comprising administering to the subject a therapeutically effective amount of the composition of claim 1.

9. The method of claim 8, wherein the composition is administered orally or sublingually.

10. The method of claim 9, wherein the composition is administered at a daily dose of 20 mg/kg/day to 50 mg/kg/day.

11. The method of claim 9, wherein the composition is administered as an oral spray, an emulsion, a tincture, a syrup, a food additive or a capsule.

12. The method of claim 8 further comprising loading the composition into a capsule.

13. The method of claim 8, wherein the composition is administered topically or transdermally.

14. The method of claim 12, wherein the composition is administered as a lotion, an oil, a cream, or a serum.

15. The composition of claim 1, wherein the first acetyl hexapeptide is selected from the group consisting of acetyl hexapeptide-3, acetyl hexapeptide-8, acetyl hexapeptide-19 and acetyl hexapeptide-24.

16. The composition of claim 1, wherein at least one of the first acetyl hexapeptide and the second acetyl hexapeptide comprises sulfur.

17. The composition of claim 1, wherein the first acetyl hexapeptide and the second acetyl hexapeptide comprise sulfur.

* * * * *